United States Patent [19]

Shoji et al.

[11] Patent Number: 5,047,560

[45] Date of Patent: Sep. 10, 1991

[54] PROCESS FOR PRODUCING HIGHLY PURE 3,3',4,4'-BIPHENYLTETRACARBOXYLIC ACID OR DIANHYDRIDE THEREOF

[75] Inventors: Fusaji Shoji, Yokohama; Nobuo Aoki, Gunma; Jun Kurita; Tsuyoshi Aoyama, both of Shibukawa; Toshiyuki Kiriyu, Gunma; Yoshinori Matsuzaki, Yokohama, all of Japan

[73] Assignees: Hitachi, Ltd.; Japan Carlit Co., Ltd.; Kanto Koatsu, all of Tokyo, Japan

[21] Appl. No.: 490,917

[22] Filed: Mar. 9, 1990

[30] Foreign Application Priority Data

Oct. 6, 1989 [JP] Japan .................. 1-260026

[51] Int. Cl.$^5$ .................. C07D 307/77; C07C 63/331
[52] U.S. Cl. .................... 549/241; 562/480; 562/483; 562/485; 562/488
[58] Field of Search .............. 549/241; 562/400, 405, 562/408, 414, 480, 483, 488, 485

[56] References Cited

U.S. PATENT DOCUMENTS

| 3,899,517 | 8/1975 | Fletcher et al. | 549/241 |
|---|---|---|---|
| 3,928,430 | 12/1975 | Mruk | 260/515 |
| 3,940,426 | 2/1976 | Italani et al. | 549/241 |
| 3,956,320 | 5/1976 | Heath et al. | 549/241 |
| 3,965,125 | 6/1976 | Meyers | 549/241 |
| 4,054,600 | 10/1977 | Johnson | 549/241 |
| 4,102,905 | 7/1978 | Williams, III et al. | 549/241 |
| 4,370,487 | 1/1983 | Meyer et al. | 549/241 |
| 4,543,416 | 9/1985 | Peters | 549/241 |
| 4,808,731 | 2/1989 | Berdahl et al. | 549/241 |
| 4,863,640 | 9/1989 | Scola | 549/241 |
| 4,912,233 | 3/1990 | Kikuchi et al. | 549/241 |

FOREIGN PATENT DOCUMENTS

| 274887 | 7/1988 | European Pat. Off. . | |
| 296636 | 12/1988 | European Pat. Off. . | |
| 249977 | 11/1986 | Japan . | |
| 257934 | 11/1987 | Japan . | |
| 1-17878 | 5/1989 | Japan | 549/241 |
| 1-197476 | 8/1989 | Japan | 549/241 |

OTHER PUBLICATIONS

Takeuchi et al., Chem. Abst 106-140112v (1987).
Kitai et al., Chem. Abst. 108-95147p (1988).
World Patent Index Database; accession no. 76-02780X, week 02 1976, Derwent Publications Ltd., London.

*Primary Examiner*—Cecilia Shen
*Attorney, Agent, or Firm*—Antonelli, Terry, Stout & Kraus

[57] ABSTRACT

Highly pure 3,3',4,4'-biphenyltetracarboxylic acid (BPTA) and dianhydride thereof (BPDA) are produced by heating crude BPTA to give BPDA, treating the BPDA with hot water to give highly pure BPTA, and in the case of highly pure BPDA, heat treating the pure BPTA to give highly pure BPDA.

7 Claims, No Drawings

PROCESS FOR PRODUCING HIGHLY PURE 3,3',4,4'-BIPHENYLTETRACARBOXYLIC ACID OR DIANHYDRIDE THEREOF

BACKGROUND OF THE INVENTION

This invention relates to a process for producing highly pure 3,3',4,4'-biphenyltetracarboxylic acid (hereinafter referred to as "BPTA") and highly pure 3,3',4,4'-biphenyltetracarboxylic dianhydride (hereinafter referred to as "BPDA"), which are starting materials for producing polyimide resins having excellent heat resistance.

BPDA has been noticed as a starting material for producing polyimide resins excellent in heat resistance. With an increase of demand for higher properties of polyimide resins, BPDA having higher purity has been demanded recently.

There have been proposed various processes for producing BPDA. One typical process comprises carrying out dehydrogenation dimerization of a dialkyl orthophthalate to produce 3,3',4,4'-biphenyltetracarboxylic acid tetraester, which is hydrolyzed to produce BPTA, followed by dehydration of BPTA. The purity of BPDA finally obtained is not always high due to contamination of a part of various impurities such as an unreacted starting material, byproducts, inorganic materials such as a catalyst and ions thereof.

Another process for producing BPTA comprises heating an aqueous solution of an alkali metal salt of 4-halogenoorthophthalic acid and an alkali hydroxide in the presence of a catalyst of metallic palladium carried on a carrier and methanol or the like as a catalyst to conduct dimerization reaction. After the reaction, the reaction solution is filtered to remove the palladium catalyst and the filtrate is added with an acid to deposit BPTA, followed by isolation of BPTA as crystals by heating and filtering with heating. The resulting BPTA is dried to give crude BPTA. The crude BPTA contains various impurities as mention above such as phthalic acid derived from the starting material, alkali metal salts, alkaline earth metal salts, and the like metal salts. There is also a process for producing BPTA by dimerization of dialkyl 4-halogenoorthophthalate in the presence of a nickel catalyst, and a co-catalyst. The purity of crude BPTA obtained in these processes is generally 85 to 90%.

Highly pure BPDA has been obtained by dehydration reaction of the crude BPTA, for example, by a dehydration process in the presence of an aliphthalic acid anhydride such as acetic anhydride, or by a process comprising subliming crude BPTA or crude BPDA with heating, followed by cooling the vapor thereof to give BPDA (Japanese Patent Unexamined Publication Nos. 61-249977 and 62-257934).

According to the former process, crude BPTA is refluxed with a large amount of an aliphthalic acid anhydride such as acetic anhydride and dehydrated to yield BPDA together with removal of impurities such as phthalic anhydride by dissolution due to a difference in the solubilities so as to increase the purity of BPDA. But this process is disadvantageous in that the handling is inconvenient due to the use of acetic anhydride, etc., having a strong irritating odor, and a production cost increases due to the consumption of a large amount of acetic anhydride, etc.

According to the latter process, the dehydration with heating and purification by sublimation are conducted. But this process is disadvantageous in that a production cost of BPDA increases due to the use of a large-scale apparatus and special control of conditions is necessary for the purification since phthalic acid, phthalic anhydride, etc. are also sublimed.

SUMMARY OF THE INVENTION

It is an object of the present invention to provide a process for producing highly pure BPTA and highly pure BPDA by a simple and economic process wherein dehydration of crude BPTA to give the acid anhydride and purification are conducted simultaneously.

The present invention provides a process for producing highly pure 3,3',4,4'-biphenyltetracarboxylic acid, which comprises heating crude 3,3',4,4'-biphenyltetracarboxylic acid preferably at a temperature of 160° to 260° C. to produce 3,3',4,4'-biphenyltetracarboxylic dianhydride, treating the resulting 3,3',4,4'-biphenyltetracarboxylic dianhydride with hot water to separate impurities by dissolution, and filtering the resulting 3,3',4,4'-biphenyltetracarboxylic acid.

The present invention also provides a process for producing highly pure 3,3',4,4'-biphenyltetracarboxylic dianhydride, which comprises heating crude 3,3',4,4'-biphenyltetracarboxylic acid preferably at a temperature of 160° to 260° C. to produce 3,3',4,4'-biphenyltetracarboxylic dianhydride, treating the resulting 3,3',4,4'-biphenyltetracarboxylic dianhydride with hot water to separate impurities by dissolution, filtering the resulting 3,3',4,4'-biphenyltetracarboxylic acid and heating the resulting 3,3',4,4'-biphenyltetracarboxylic acid preferably at a temperature of 200° to 260° C.

DESCRIPTION OF THE PREFERRED EMBODIMENTS

According to the present invention, crude BPTA is placed in a reactor equipped with a trap for removing unreacted compounds and byproducts such as phthalic anhydride and heated preferably at a temperature of 160° to 260° C. With the dehydration of BPTA, dehydration of phthalic acid also takes place to produce by sublimation phthalic anhdyride, which is separated by the trap, etc. In order to remove phthalic acid and the like effectively, it is preferable to heat the crude BPTA in fine powder.

The heating is conducted at a temperature of preferably 160° to 260° C., more preferably 200° to 240° C., most preferably about 220° C. The dehydration efficiency is better in the temperature range of 200° to 260° C. When the temperature is lower than 160° C., the dehydration efficiency decreases undesirably. On the other hand, when the temperature is higher than 260° C., there is a fear of coloring. Further, by the heat treatment at 160° to 260° C., crystals of BPDA grow to give larger grains, which results in making the subsequent hot water treating and filtering steps remarkably easy.

The heating time is preferably 1 to 8 hours, more preferably 2 to 4 hours.

The BPDA obtained by the heat treatment is enhanced in the purity considerably due to removal of phthalic acid or phthalic anhydride obtained by dehydration. The resulting BPDA is treated with hot water, for example, distilled water heated preferably at about 95° to 105° C. By the treatment with hot water, BPDA is changed to BPTA and at the same time trace amounts of phthalic acid, various metallic ions and anions are separated by a difference in solubilities and removed by filtration.

More concretely, the hot water treatment is carried out by stirring the BPDA obtained with hot water heated at 95° C. to 105° C., the temperature of 105° C. being able to be raised under pressure, e.g. upto 120° C. or higher. As a result, impurities are dissolved in the hot water by the difference in solubilities, while BPTA is deposited as crystals. By filtering the crystals of BPTA and washing with hot or cold water, the impurities are almost completely removed.

The resulting BPTA is sufficiently high in the purity, for example, about 98 to 99.6%. If necessary, the resulting BPTA can be heated with distilled water to about 100° C., followed by filtration at about 100° C. to give more highly pure BPTA crystals.

In order to obtain the highly pure BPDA, the resulting crystals of highly pure BPTA is heated preferably at 200° to 260° C.

When crude BPTA not subjected to the heat treatment is simply washed with water or hot water, filtration is difficult due to very fine particles. Further, the resulting liquid becomes a paste-like state obtained by dissolving dogtooth violet starch in water, which results in making the handling difficult.

In contrast, when BPDA obtained by heat treatment is washed with hot water, hydrolysis takes place to deposit crystals of BPTA with larger particle size, which results in making the filtration and washing steps easier.

The thus obtained BPDA, that is, BPDA obtained by one cycle of steps of heat treatment-washing with hot water-heat treatment has a sufficiently high purity for usual use, that is, 99.5% or higher and upto near 100%. If more highly pure BPDA is required, a step of washing with water is added between the step of washing with hot water and the step of heat treatment. The purity of the resulting BPDA becomes 99.8% or more, and metallic ions and halogen ions become 1 ppm or less. Such particularly highly pure BPDA can be used as a starting material for products such as semiconductors requiring high reliability.

According to the present invention, BPTA obtained by heat treating crude BPTA to give BPDA, which is then washed with hot water to remove impurities, is highly pure. Further, by heat treating the highly pure BPTA, highly pure BPDA is obtained simply and economically.

The present invention is illustrated by way of the following Examples, in which all parts and percents are by weight unless otherwise specified.

EXAMPLE 1

(1) Preparation of biphenyltetracarboxylic acid

In a reactor equipped with a stirrer and a heating apparatus, 69 parts of aqueous solution of sodium 3,3',4,4'-biphenyltetracarboxylate (containing 5.4% of BPTA and 4.2% of phthalic acid) obtained by dimerization of sodium 4-chlorophthalate was placed. Then, 14 parts of concentrated hydrochloric acid was added thereto with stirring to deposit crude BPTA with heating, followed by filtration while hot. The resulting white cake in an amount of 7.2 parts together with 36 parts of water was placed again in the reactor and heated with stirring, followed by hot filtration. The thus obtained white cake in an amount of 4.7 parts was dried with hot air at 120° C. for 5 hours to give 2.6 parts of crude 3,3',4,4'-biphenyltetracarboxylic acid (BPTA) in white particles having a purity of 95% and containing 2% of phthalic acid.

(2) Purification and Dehydration

The crude BPTA thus obtained was finely powdered and placed in a heating device equipped with a cooling trap at an exhaust vent. The crude BPTA was subjected to dehydration with heating at 220° C. for 2 hours under slight suction. After cooling, the resulting crude BPDA in white powder in an amount of 2.2 parts was placed in a reactor equipped with a stirrer and a heating apparatus together with 26 parts of water and heated at 102° to 104° with stirring. After cooling, the contents of the reactor were filtered to give crystals. The crystals were heated together with 26 parts of water with heating at 102° to 104° C. again. After cooling, crystals of BPTA were obtained by filtration. The resulting crystals in an amount of 3.8 parts was dried with hot air at 120° C. for 5 hours to give a white powder of BPTA having a purity of 99.8% or more.

The resulting BPTA was subjected to dehydration with heating at 220° C. for 3 hours to give 2.1 parts of purified BPDA in white powder. The BPDA had a purity of 99.8% or more and contained no phthalic anhydride and sodium ions and chlorine ions in amounts of 1 ppm or less, respectively.

EXAMPLES 2 to 4

(1) Preparation of biphenyltetracarboxylic acid

Crude 3,3',4,4'-biphenyltetracarboxylic acid (BPTA) in an amount of 28 parts was prepared in the same manner as described in Example 1(1). The BPTA had a purity of 96% and contained phthalic acid in an amount of 1%.

(2) Purification and Dehydration

① Purification of crude BPTA

Finely powdered crude BPTA in amounts of 3.9 parts (Example 2), 5.2 parts (Example 3) and 3.9 parts (Example 4) was placed in a heating apparatus equipped with a cooling trap at an exhaust vent, respectively, and dehydrated with heating at 210°, 230° and 250° C., respectively, for 2 hours. After cooling, white powdery crude BPDA was obtained in amounts of 3.3 parts, 4.5 parts and 3.4 parts, respectively. These amounts of crude BPDA were placed in reactors equipped with a stirrer and a heating apparatus together with 40 parts, 54 parts and 40 parts of water, respectively, and heated at 93°-98° C., 95°-100° C., and 105°-110° C., respectively with stirring. After cooling, filtration was carried out to give crystals, respectively. These crystals were heated again together with 40 parts, 54 parts and 40 parts, respectively, of water with stirring. After cooling, filtration was carried out to give crystals in amounts of 5.7 parts, 7.8 parts and 5.9 parts, respectively. These crystals were dried with hot air at 120° C. for 5 hours to give BPTA white powders having a purity of 99.8% or more.

② Dehydration of BPTA

The thus obtained BPTA powders were subjected to dehydration with heating at 210° C. (Example 2), 230° C. (Example 3) and 250° C. (Example 4) for 3 hours in the same manner as described in Example 1 to give purified BPDA crystals in amounts of 3.1 parts, 4.3 parts and 3.3 parts, respectively. These crystals had a purity of 99.8% or more and contained no phthalic anhydride.

Ion contents in Examples 2 to 4 were 1 ppm or less in both sodium ion and chlorine ion contents.

COMPARATIVE EXAMPLE 1

In a closed type reactor having therein a heating apparatus at a lower portion, a plate-like cooling face of a cooling apparatus at an upper portion and a gas exhaust vent at a top, one part of crude BPTA as used in Example 1 was placed and heated under reduced pressure. After heating at 200° C. for 2 hours under 40 mmHg, the resulting BPDA was further heated at 300° C. for 1 hour under 20 mmHg. Yellowish crystals of BPDA deposited on the cooling face were recovered in an amount of 0.9 part. The BPDA had a purity of 99.2% and contained 0.5% of phthalic anhydride.

As mentioned above, according to the present invention, highly pure BPTA and highly pure BPDA which are useful as starting materials for high purity polyimide can be obtained effectively and economically.

What is claimed is:

1. A process for producing highly pure 3,3',4,4'-biphenyltetracarboxylic acid, which comprises heating crude 3,3',4,4'-biphenyltetracarboxylic acid in the form of fine powder at 160° C.–260° C. to produce 3,3',4,4'-biphenyltetracarboxylic dianhydride, treating the resulting 3,3',4,4'-biphenyltetracarboxylic dianhydride with hot water to separate impurities by dissolution, and filtering the resulting 3,3',4,4'-biphenyltetracarboxylic acid.

2. A process according to claim 1, wherein the heating is carried out at a temperature of 200° C. to 260° C.

3. A process according to claim 1, wherein the hot water treatment is carried out by stirring the 3,3',4,4'-biphenyltetracarboxylic dianhydride with hot water, dissolving impurities and filtering the resulting 3,3',4,4'-biphenyltetracarboxylic acid to remove the impurities.

4. A process for producing highly pure 3,3',4,4'-biphenyltetracarboxylic dianhydride, which comprises heating crude 3,3',4,4'-biphenyltetracarboxylic acid in the form of fine powder at 160° C.–260° C. to produce 3,3',4,4'-biphenyltetracarboxylic dianhydride, treating the resulting 3,3',4,4'-biphenyltetracarboxylic dianhydride with hot water to separate impurities by dissolution, filtering the resulting 3,3',4,4'-biphenyltetracarboxylic acid and heating the resulting 3,3',4,4'-biphenyltetracarboxylic acid.

5. A process according to claim 4, wherein the last heat treatment is carried out at a temperature of 200° to 260° C.

6. A process according to claim 4, wherein the hot water treatment is carried out by stirring the 3,3',4,4'-biphenyltetracarboxylic dianhydride with hot water, dissolving impurities and filtering the resulting 3,3',4,4'-biphenyltetracarboxylic acid to remove the impurities.

7. A process according to claim 4, wherein a step of washing with water is inserted between the step of treatment with hot water and the step of heat treatment.

* * * * *